(12) United States Patent
Castaneda et al.

(10) Patent No.: US 8,790,378 B2
(45) Date of Patent: Jul. 29, 2014

(54) DISTAL RADIUS FRACTURE FIXATION PLATE WITH INTEGRATED AND ADJUSTABLE VOLAR ULNAR FACET SUPPORT

(75) Inventors: Alfredo Castaneda, Miami, FL (US); Eduardo A. Ampuero, Miami, FL (US)

(73) Assignee: Biomet C.V., Gibraltar (GI)

( * ) Notice: Subject to any disclaimer, the term of this patent is extended or adjusted under 35 U.S.C. 154(b) by 126 days.

(21) Appl. No.: 13/364,513

(22) Filed: Feb. 2, 2012

(65) Prior Publication Data
US 2013/0204307 A1 Aug. 8, 2013

(51) Int. Cl.
*A61B 17/80* (2006.01)

(52) U.S. Cl.
USPC ........... 606/285; 606/283; 606/284; 606/286; 606/282

(58) Field of Classification Search
USPC .................................. 606/283–286, 74, 282
See application file for complete search history.

(56) References Cited

U.S. PATENT DOCUMENTS

| | | | |
|---|---|---|---|
| 3,741,205 A | 6/1973 | Markolf et al. | |
| 3,842,825 A | 10/1974 | Wagner | |
| 4,219,015 A | 8/1980 | Steinemann | |
| 4,388,921 A | 6/1983 | Sutter et al. | |
| 4,573,458 A | 3/1986 | Lower | |
| 4,955,886 A | 9/1990 | Pawluk | |
| 4,973,332 A | 11/1990 | Kummer | |
| 5,057,109 A | 10/1991 | Olerud | |
| 5,147,361 A | 9/1992 | Ojima et al. | |
| 5,616,144 A | 4/1997 | Yapp et al. | |
| 5,647,712 A | 7/1997 | Demirdogen et al. | |
| 5,772,662 A | 6/1998 | Chapman et al. | |
| 5,954,722 A | 9/1999 | Bono | |
| 6,004,353 A | 12/1999 | Masini | |
| 6,123,709 A | 9/2000 | Jones | |
| 6,206,881 B1 | 3/2001 | Frigg et al. | |
| 6,364,882 B1 | 4/2002 | Orbay | |

(Continued)

FOREIGN PATENT DOCUMENTS

| | | |
|---|---|---|
| DE | 8628766 | 12/1986 |
| EP | 0206767 | 12/1986 |

(Continued)

OTHER PUBLICATIONS 2.4 mm Variable Angle LCP Distal Radius System. For fragment-specific fracture fixation with variable angle locking technology. Technique Guide, Synthes, 2008.

*Primary Examiner* — Andrew Yang
*Assistant Examiner* — Olivia C Chang
(74) *Attorney, Agent, or Firm* — Gordon & Jacobson, PC

(57) ABSTRACT

A volar distal radius plate includes a shaft and a head. The head includes a radial side that seats below the volar rim, and an ulnar side with two extending tabs that provide a buttress support to ulnar fragments from the volar rim. The tabs are contoured to be atraumatic to the overlying soft tissue. The tabs can be readily re-orientated to better approximate the volar rim and provide close support to the volar fragments. Each tab includes a single hole specifically sized to closely receive a K-wire in a fixed angle orientation, and which permits the K-wire to apply a bending load to a tab in situ to bend the tab about a lower recess between the tab and the remainder of the head. Therefore, the plate does not require a dedicated bender. The tabs can also accommodate sutures.

23 Claims, 3 Drawing Sheets

(56) References Cited

U.S. PATENT DOCUMENTS

| | | |
|---|---|---|
| 6,454,769 B2 | 9/2002 | Wagner et al. |
| 6,506,191 B1 | 1/2003 | Joos |
| 6,565,570 B2 | 5/2003 | Sterett et al. |
| 6,623,486 B1 | 9/2003 | Weaver et al. |
| 6,652,530 B2 | 11/2003 | Ip et al. |
| 6,712,820 B2 * | 3/2004 | Orbay .................... 606/286 |
| 6,786,909 B1 | 9/2004 | Dransfeld et al. |
| 6,866,665 B2 | 3/2005 | Orbay |
| 7,189,237 B2 | 3/2007 | Huebner |
| 7,250,053 B2 | 7/2007 | Orbay |
| 7,335,204 B2 * | 2/2008 | Tornier .................... 606/284 |
| 7,604,657 B2 | 10/2009 | Orbay et al. |
| 7,935,126 B2 | 5/2011 | Orbay et al. |
| 7,951,176 B2 | 5/2011 | Grady, Jr. et al. |
| 8,021,402 B2 | 9/2011 | Martin et al. |
| 8,469,999 B2 | 6/2013 | Gonzalez-Hernandez |
| 2005/0085818 A1 | 4/2005 | Huebner |
| 2005/0234458 A1 | 10/2005 | Huebner |
| 2007/0093837 A1 | 4/2007 | Bohrmann et al. |
| 2007/0233111 A1 * | 10/2007 | Orbay et al. .................... 606/69 |
| 2008/0140127 A1 | 6/2008 | Vasta et al. |
| 2009/0018587 A1 | 1/2009 | Bottlang |
| 2009/0143825 A1 | 6/2009 | Graham |
| 2009/0275987 A1 | 11/2009 | Graham et al. |
| 2010/0057086 A1 | 3/2010 | Price et al. |
| 2011/0118795 A1 | 5/2011 | Hashmi et al. |

FOREIGN PATENT DOCUMENTS

| | | |
|---|---|---|
| FR | 742618 | 3/1933 |
| GB | 2477086 | 7/2011 |
| WO | WO 89/04150 | 5/1989 |
| WO | WO 97/09000 | 3/1997 |
| WO | WO 01/30251 | 5/2001 |

* cited by examiner

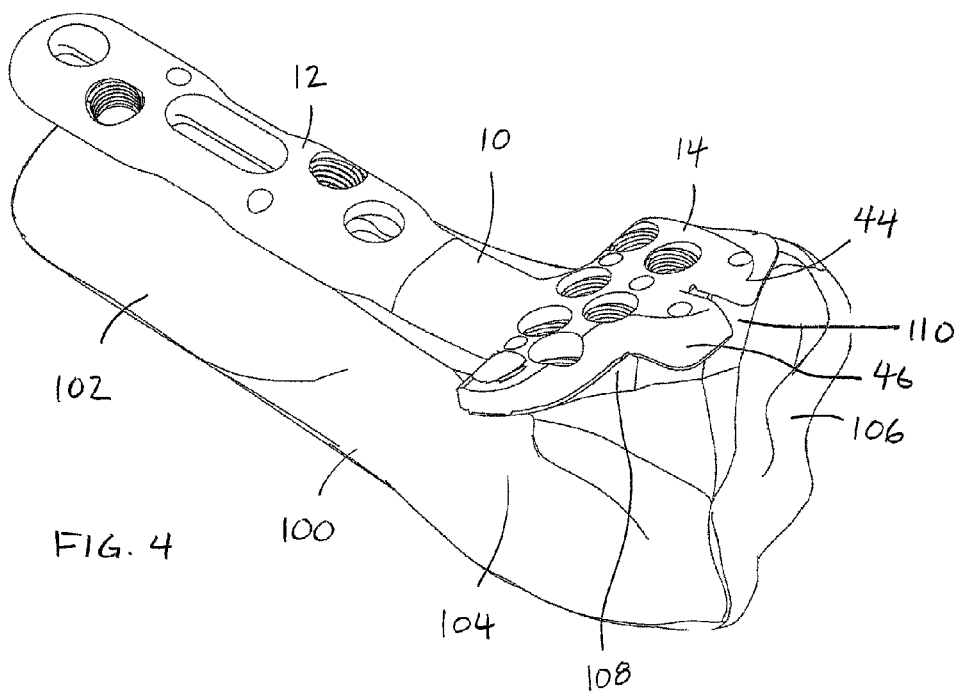
FIG. 4
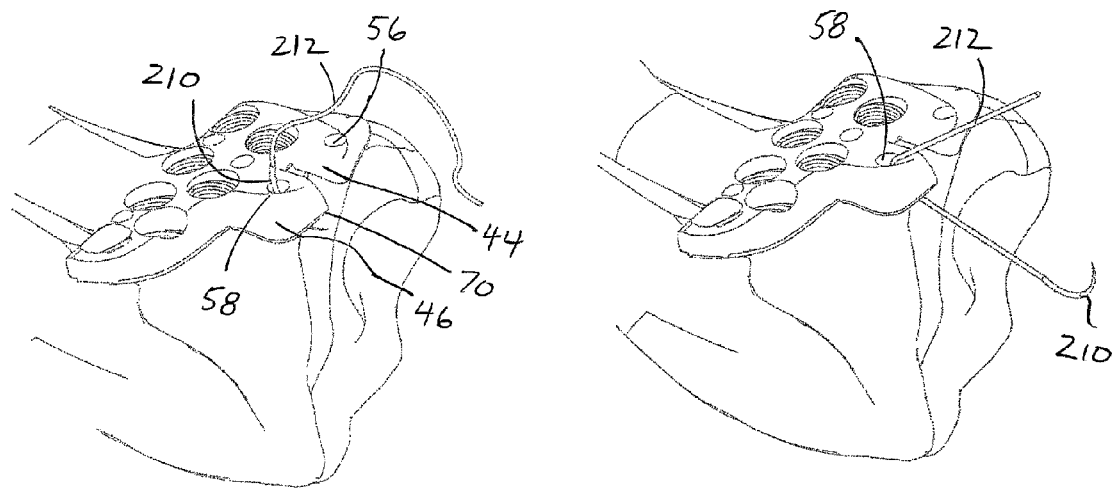
FIG. 9
FIG. 10

DISTAL RADIUS FRACTURE FIXATION PLATE WITH INTEGRATED AND ADJUSTABLE VOLAR ULNAR FACET SUPPORT

BACKGROUND OF THE INVENTION

1. Field of the Invention

This invention relates broadly to surgical implants. More particularly, this invention relates to a bone fracture fixation system for distal radius fractures.

2. State of the Art

Fracture to the metaphyseal portion of a long bone can be difficult to treat. Improper treatment can result in deformity and long-term discomfort.

By way of example, a Colles' fracture is a fracture resulting from compressive forces being placed on the distal radius, and which causes backward or dorsal displacement of the distal fragment and radial deviation of the hand at the wrist. Often, a Colles' fracture will result in multiple bone fragments which are movable and out of alignment relative to each other. If not properly treated, such fractures may result in permanent wrist deformity and limited articulation of the wrist. It is therefore important to align the fracture and fixate the bones relative to each other so that proper healing may occur.

Alignment and fixation of a metaphyseal fracture (occurring at the extremity of a shaft of a long bone) are typically performed by one of several methods: casting, external fixation, pinning, and plating. Casting is non-invasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist bones, it may nevertheless be difficult in certain fractures to first provide the bones in proper alignment. In addition, external fixators are often not suitable for fractures resulting in multiple bone fragments. Pinning with K-wires (Kirschner wires) is an invasive procedure whereby pins are positioned into the various fragments. This is a difficult and time consuming procedure that provides limited fixation if the bone is comminuted or osteoporotic. Plating utilizes a stabilizing metal plate typically placed against the side of a bone, and screws extending from the plate into holes drilled in the bone fragments to provide stabilized fixation of the fragments. However, many currently available plate systems fail to provide desirable alignment and stabilization.

The distal radius exhibits a concave shape extending from the shaft, which reaches an inflection point at a so-called watershed line followed by a convex like form at its most prominent feature, the volar rim. With a distal radius fracture, the complex shape of the distal radius, including the prominent volar rim of the lunate fossa, relatively flat volar rim of the scaphoid fossa, and the sometimes prominent base of the styloid process should be accommodated. Furthermore, the ligaments extending from the volar side of the distal radius to the intercarpal bones must not be irritated or distressed. Moreover, a fixation device should provide desirable alignment and stabilization of the bone structure proximate the articular surface of the distal radius.

Co-owned U.S. Pat. No. 7,250,053 to Orbay discloses a volar plate for the distal radius that accommodates the anatomy. The plate includes a head for placement at the metaphysis and a shaft for extension along the diaphysis. The head and shaft each include holes for receiving fasteners to couple the plate to the bone. The holes in the head are threaded fixed angle holes oriented to extend the shaft of the fasteners in a spatial distribution through the bone about the articular surface to provide significant support and early mobility. In addition, the top portions of the plate are such that they provide a buttress support for the fragment while providing a smooth contour to minimize soft tissue interaction and not creating a prominent sharp edge nearest the inflexion point or 'watershed line' of the volar rim. This is achieved by a contoured shape that blends back into the anatomy without extending into the articular surface. The lower surface of the ulnar side of the head of this plate is contoured to accommodate the concave shape of the distal radius below the watershed line. It is specifically indicated that the watershed line is not to be violated by the plate.

However, volar ulnar facet fractures occur in the distal portion of the concave form of the distal radius and require additional fixation. The fractures may involve displaced avulsions, shear fractures and small fragments that are in the vicinity of the prominent portion of the volar rim. These fractures are difficult to treat with existing hardware since most available hardware could interfere with surrounding soft tissue and/or increase the likelihood impinging on the articular surfaces of the distal radius.

US Pub. No. 2009/0275987 to Graham proposes various plates and adjunct extenders that can be physically attached to the plates with screws to provide supplementary anatomical support. The extenders are not ideally shaped to limit interference with soft tissue. In addition, this type of support requires the attachment of very small plates to the primary plate and can be difficult to work with, particularly in the operating room and during a surgical procedure. There is no easy and reliable way to fit the extenders to the anatomy during the procedure.

SUMMARY OF THE INVENTION

A volar distal radius plate is provided having a shaft for placement on the diaphysis of the distal radius bone, and a head angled relative to the shaft and shaped for low profile placement on the metaphysis of the distal radius bone. The plate has a lower bone contacting surface and an opposite upper surface.

The head of the plate is shaped to primarily seat below the boney crest inflexion point of the 'watershed line' at the distal radius. The head and shaft each include holes for receiving fasteners to couple the plate to the bone. The holes in the head are threaded, fixed angle holes, arranged in two rows. The holes are oriented to extend screws in a spatial distribution through the bone and about the articular surface of the wrist socket to provide significant support. The threaded fixed angle holes are provided within the head to be located below the boney crest or watershed line of the distal radius.

The radial side of the plate seats completely below the watershed line. The ulnar (or medial) side of the plate is provided with two smoothly contoured and chamfered distally extending tabs for extension over and beyond the watershed line when the plate is positioned on the bone. The tabs provide a buttress support over the volar ulnar facet. The tabs each have a smoothly contoured upper surface that is adapted to be atraumatic to the soft tissue and thereby minimize soft tissue irritation. In addition, the tabs can be readily re-orientated to approximate the volar rim and provide close support. In order to re-orient the tabs, the tabs are provided with respective lower recesses, preferably as an undercut at the junction of the tabs and the remainder of the head plate; i.e., in a preferred embodiment, from the lower surface of the plate, the undercut and distal edge of the lateral side of the plate are in alignment. The recesses allow each tab to be contoured independently to fit the patient anatomy. Each tab is provided with a single hole specifically sized to closely receive a K-wire in a fixed angle orientation. This permits a K-wire to apply a bending load to a tab in situ to bend the tab about its lower recess into a new orientation to best match the patient anatomy and provide support. Therefore, the plate does not require a dedicated bender. In addition, the hole in each tab is spaced relative to the distal peripheral edge of the tab to accommodate passage of a suture needle completely therethrough.

BRIEF DESCRIPTION OF THE DRAWINGS

FIG. 4 is a perspective view of the plate of FIG. 1 shown on a portion of a distal radius bone.

FIGS. 9 and 10 are perspective views illustrating the advancement of a suture needle and suture through the hole in an extension tab to secure soft tissue at the joint capsule.

DETAILED DESCRIPTION OF THE PREFERRED EMBODIMENTS

Figure 1:
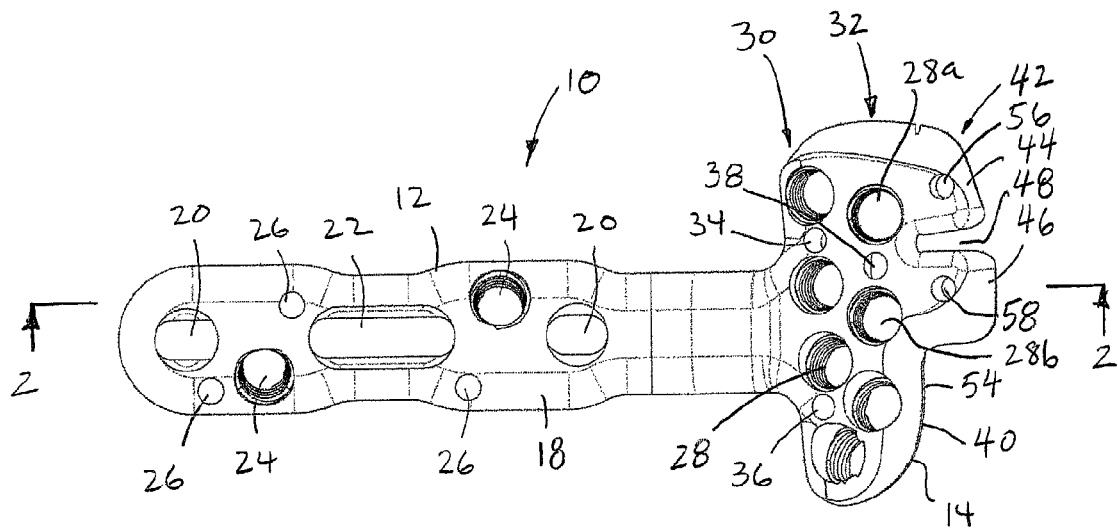
FIG. 1 is a top view of a distal radius plate according to the invention.

Turning now to FIGS. 1 through 4, a bone plate 10 for stabilization of a fracture of a distal radius bone 100 is shown. The plate 10 includes a shaft 12 for placement on the diaphysis 102 of the distal radius bone 100, and a head 14 at a transverse orientation relative to the shaft for placement on the metaphysis 104. The plate includes a bone contacting lower surface 16 and an opposite upper surface 18. The head is in angled upward relative to the shaft when the lower surface 16 of the shaft is positioned substantially horizontal and face down in contact with the diaphysis of the radius bone.

The shaft 12 and head 14 each include holes for receiving fasteners to couple the plate 10 to the bone 100. The shaft 12 preferably includes a combination of compression holes 20, 22 and non-compression fixed angle, threaded holes 24. The compression holes preferably comprise both circular holes 20 and elongate slots 22. Preferably, the holes 20, 22, 24 comprise the system of holes described in co-owned and co-pending U.S. Ser. No. 13/313,350, filed Dec. 7, 2011, which is hereby incorporated by reference herein in its entirety. Holes of another design for suitable fasteners may also be used; however, it is preferable that any provided holes and arrangement thereof include both circular holes and slots, and that such circular holes include a combination of compression holes for compression fasteners and fixed angled holes such as can accommodate a fastener with a threaded head in a fixed orientation. The plate may also include one of more K-wire holes 26 to closely receive respective K-wires for temporary fixation of the shaft 12 of the plate relative to the bone 100.

The holes 28 in the head of the plate 14 are threaded, fixed angle holes, with the threads of each hole defining a respective fixed axis for a fastener inserted therethrough. In a preferred embodiment, the threaded holes 28 are preferably of a same configuration and size as the threaded holes 24, and thus capable of receiving and fixing a common fastener therewith. One exemplar fastener 150 is shown in phantom in FIG. 2. The holes 28 are preferably arranged in two rows; a relatively proximal row 30 and a relatively distal row 32, the rows 30, 32 being acutely angled relative to each other. In a preferred embodiment, the proximal row 30 of holes includes four threaded holes 28, and the distal row 32 includes three threaded holes 28 preferably arranged in an offset from the proximal row 30 such that the shafts of fasteners inserted in the proximal row 30 can extend distally between the shafts of the fasteners inserted in the distal row 32 in an interleaved manner. More preferably, when the plate is positioned on the bone at the intended location, the fasteners 150 extend into the bone in a spatial distribution about the articular surface 106 (FIG. 4) of the wrist socket to provide subchondral support. All the threaded fixed angle holes 28 within the head 14 of the plate are provided to be located in the subchondral bone below the inflexion point of the watershed line (seen also in FIG. 6) on the volar side of the distal radius. Preferred locations of the threaded holes 28 relative to the volar distal radius and preferred axial orientations of such threaded holes are described in detail in U.S. Pat. No. 7,294,130, which is hereby incorporated by reference herein in its entirety.

K-wire holes are also preferably provided relative to the threaded holes in the head of the plate. Two K-wire holes 34, 36 are provided between respective sets of adjacent holes in the proximal row 30 of threaded holes. The K-wire holes 34, 36 are sized to closely receive a K-wire such that an appropriately sized K-wire inserted therethrough is retained at a fixed angle relative to the plate 10 by the sidewalls of the respective K-wire hole. Such holes can be used for temporary fixation of the plate to the bone. Further, the K-wire, whether or not providing such temporary fixation, can be examined under fluoroscopy to analyze its trajectory relative to the bone anatomy and thereby provide information with respect to the apparent trajectory of fasteners through the adjacent threaded holes. In this manner, the K-wires inserted through the K-wire holes provided feedback as to the appropriate placement of the plate prior to drilling larger holes in the bone for the relatively larger fasteners. An additional K-wire hole 38 is preferably provided between two of the holes in the distal row 32. In addition, other small holes, such as 38 can be provided to the head of the plate. Such other small holes may be additional K-wire holes of the types described for the purpose of guiding a K-wire or the plate relative to the K-wire, or may be of the same or different structure so as to be otherwise adapted as anchor holes for suture to secure bone fragments and soft tissue relative to the plate.

Figure 2:
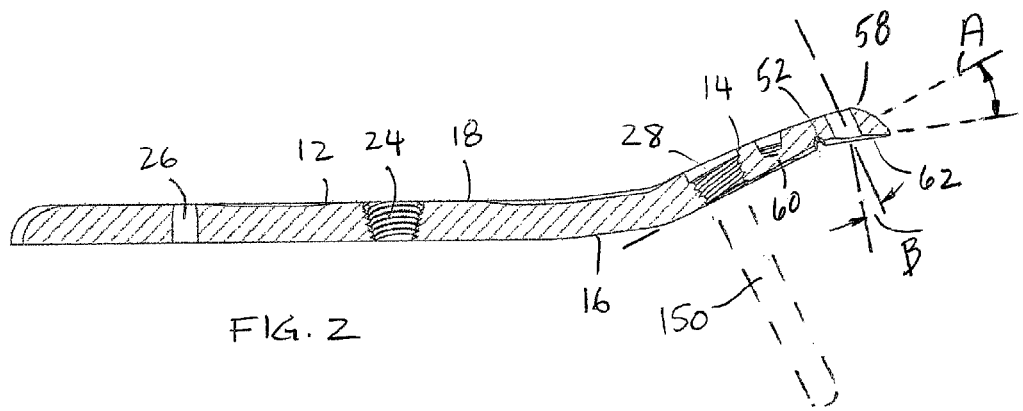
FIG. 2 is a longitudinal section view along line 2-2 in FIG. 1.
Figure 3:
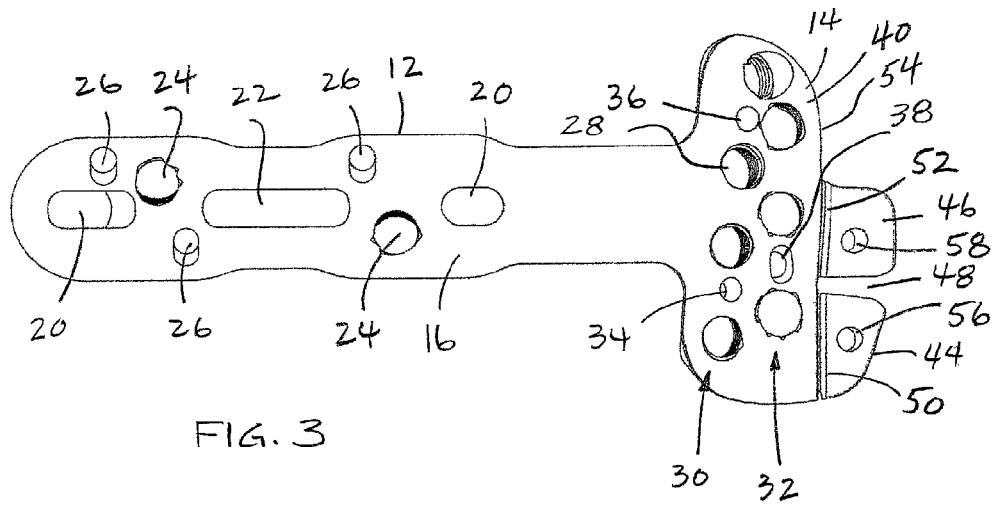
FIG. 3 is a bottom view of the plate of FIG. 1.
Figure 5:
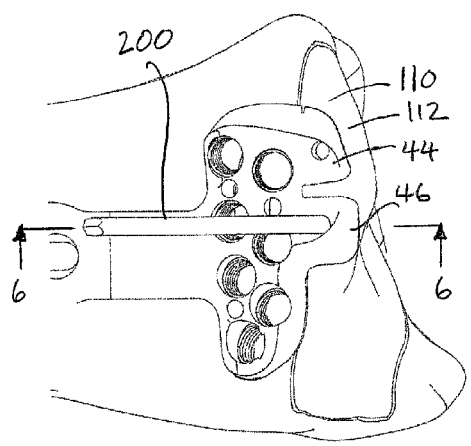
FIG. 5 is a top view and a FIG. 6 is a longitudinal section view along line 6-6 in FIG. 5, both illustrating insertion of a K-wire into a hole in an extension tab of the distal radius plate prior to bending of the tab.
Figure 7:
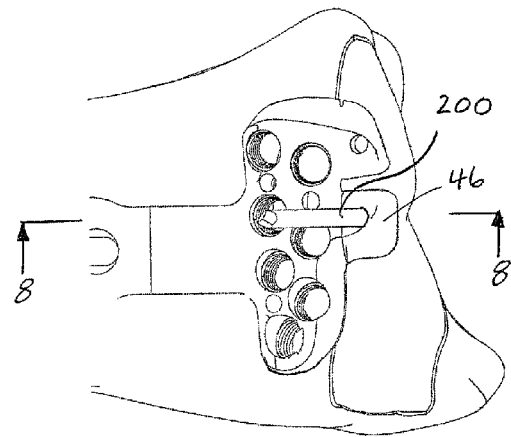
FIG. 7 is a top view and a FIG. 8 is a longitudinal section view along line 8-8 in FIG. 7, both illustrating use of a K-wire for bending of the extension tab of the distal radius plate with the K-wire inserted into the hole in the extension tab.

Referring to FIGS. 1 and 3, the radial side 40 of the plate 10 is tapered to a distal edge 54 and sized and shaped to seat completely below the 'watershed' inflexion line 108 of the boney crest. In distinction, the ulnar (i.e., medial) side 42 of the distal edge of the plate is provided with two distally extending tabs 44, 46 separated from each other by a space 48. As shown, the radial side 40 is free and absent of any such tabs. While the tabs 44, 46 extend from the ulnar (i.e., medial) side 42 of the distal edge, the tabs do not extend the lateral dimension of the head of the plate; the entire extension is preferably distal and displaced to the ulnar side. The tabs 44, 46 extend approximately 5 mm beyond the distal end 54 of the plate such that the tabs 44, 46 extend beyond the 'watershed' inflexion line of the distal radius bone when the plate is properly positioned on the bone in order to provide a support to the volar fragment, and particularly the ulnar facet 110 thereof (FIGS. 4 and 5). This allows the tabs 44, 46 to claw or buttress the volar fragment. In a preferred embodiment, the tabs 44, 46 may be considered to be located as an ulnar side tab 44 and an intermediate tab 46, with 'intermediate' defining a location between the ulnar and radial sides of the distal radius when the plate is positioned on the volar side of the distal radius (and not a relative location between other tabs). The ulnar side tab 44 is located distally in front of the medialmost (ulnar side) threaded hole 28*a* of the distal row 32 of threaded holes 28, and the intermediate tab 46 is located distally in front of the central threaded hole 28*b* of the distal row 32 of threaded holes 28 (FIG. 1). The tabs 44, 46 each have a smoothly contoured and chamfered upper surface which tapers toward the medial side of the relatively ulnar side tab 44 and toward the lateral side of the intermediate tab 46. This provides the upper surface of the tabs 44, 46 with an atraumatic soft tissue contacting surface that minimizes soft tissue irritation. Referring specifically to FIG. 2, the lower surfaces 62 of the tabs are angled relative to the lower surface 60 at the remainder of the lower surface of the head 14. That is, while the remainder of the lower surface 60 of the head 14 is configured to seat in the concavity on the bone below the 'watershed' inflexion line of the distal radius, the tabs 44, 46 are configured to extend over the watershed line and generally parallel to the volar rim 110. Thus, the lower surfaces 62 of the tabs 44, 46 extend out of orientation with the lower surface 60 of the remainder of the head by an acute angle shown at A. Angle A is preferably between 26° and 30°.

Figure 6:
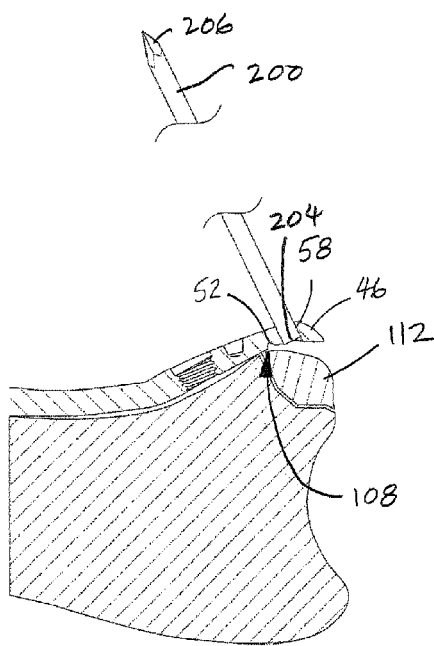
Figure 8:
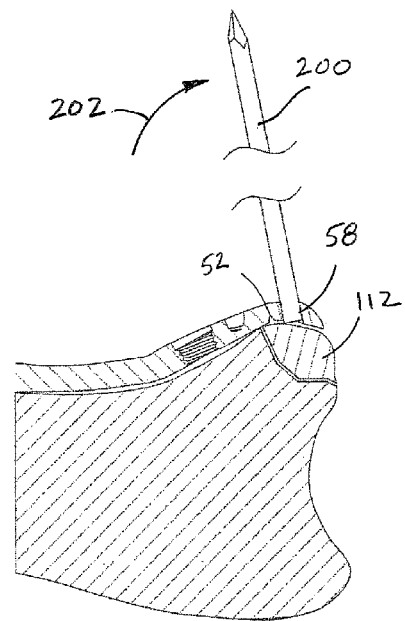

Referring to FIGS. 2 and 3, in accord with the invention, the tabs 44, 46 can be readily re-orientated in situ to better approximate the volar rim 110 and provide close support to a fragment of the volar rim. Each tab 44, 46 is provided with a single K-wire hole 56, 58 each defined by a cylindrical sidewall and specifically sized to closely receive a 1.6 mm K-wire in a fixed angle orientation. A fixed angle orientation is one in which the K-wire is retained coaxial with or within 5°, and more preferably within 3°, of the axis of the K-wire hole. With too much play between the K-wire and plate, the K-wire cannot positively engage the hole to provide accurate bending of the tabs in accord with the desired operation of the system. With respect to K-wire hole 58, the hole has an approximate diameter of 1.6 mm to provide the necessary clearance for passage of the K-wire. The axes of the holes 56, 58 in the tabs 44, 46 are oblique relative to the lower surface 16 at the tabs, as shown by angle β (FIG. 2) and also seen in FIG. 3. The tabs 44, 46 are provided with respective lower recesses 50, 52 preferably formed as an undercut at the junction of the tabs and the remainder of the head of the plate; i.e., in a preferred embodiment, from the lower surface 16 of the plate, the recesses 50, 52 and distal edge 54 of the radial side 40 of the plate are in alignment. The recesses 50, 52 reduce the cross-sectional area moment of inertia at the junction between the tabs 44, 46 and the remainder of the head 14 without requiring that the width of the tabs be reduced. That is, it is preferable that the junctions between the tabs and the remainder of the head are not reduced in the width (in a medial-lateral direction) relative to the respective tabs. As a result of the reduced cross-sectional area moment of inertia at the junctions, when a force is applied to a tab, all plastic deformation will be located at the reduced cross-sectional area—leaving the tab and the K-wire hole without deformation—and the tabs 44, 46 will be re-oriented about an axis in alignment with the radial side distal edge 54. The recesses 50, 52 allow each tab 44, 46 to be contoured independently of the other to fit the patient anatomy. Referring to FIGS. 5-8, with the K-wire 200 inserted into the K-wire hole 58 of tab 46, the K-wire 200 is able to apply a bending load to the tab 46 in situ to bend the tab about its lower recess 52, e.g., in the direction of arrow 202, into a new orientation to best match the patient anatomy and provide support for the ulnar facet of the volar rim 110. Therefore, the plate does not require a dedicated bender. Moreover, the K-wire 200 is an extremely unobtrusive tool for use during the surgical procedure, providing excellent visibility to the remainder of the plate 10 and surgical wound during the bending operation to allow the surgeon to visually confirm plate-to-anatomy conformation. Using the K-wire 200, the tabs 44, 46 can be bent independently, quickly, and accurately to fit the anatomy. Referring to FIG. 6, it is preferable that, for purposes of tab bending, a K-wire 200 be inserted blunt side 204 down toward the bone to prevent the sharpened tips 206 at the opposite end from catching the bone and inhibiting bending or inadvertently displacing loose bone fragments.

In addition, the K-wire holes 56, 58 can be used for stable, temporary fixation of a volar rim fragment relative to the plate 10 and the remainder of the distal radius 100 with a K-wire. In such use, one or more K-wires are preferably inserted via a drill, with the sharpened side 206 of the K-wire inserted down into the bone.

Turning now to FIGS. 9 and 10, the tabs 44, 46 and K-wire hole 56, 58 in each tab is spaced relative to the distal peripheral edge 70 of the respective tab to accommodate passage of a ⅜ inch circle suture needle 210 completely therethrough. For this purpose and other reasons, the holes 56, 58 are each displaced preferably approximately 2.5 mm from the edge 70 of the respective tabs 44, 46. In addition, the tabs each have a maximum thickness of 2.0 mm. In view of this structure, and by way of example, a ⅜ inch circle ETHICON P3 suture needle can be passed completely through the hole 58 in tab 46. This allows the tab 46 to receive suture 212 to capture the smallest bone fragment and further repair the joint capsule at the fracture site.

The plate provides stability to volar distal radius fractures, particularly where support of the volar rim is desirable. The tabs extending from the ulnar side of the plate do not require any attachment to the plate at the time of the surgical procedure; they are integrated into the plate preventing the potential for otherwise loose components to drop into the surgical wound, reduce implantation time, and eliminate potential difficulties. Further, the tabs are easily bent to confirm to the underlying boney anatomy to best buttress the volar rim and/or place suture holes in a location suitable for soft tissue repair. Also, such tabs are designed to be non-irritating to surrounding soft tissue.

There have been described and illustrated herein embodiments of a volar distal plate. While particular embodiments of the invention have been described, it is not intended that the invention be limited thereto, as it is intended that the invention be as broad in scope as the art will allow and that the specification be read likewise. That is, while an embodiment with a specified number of threaded holes in the plate is described, it is appreciated that a greater or fewer number of threaded holes can be provided in the head of the plate. By way of example, the distal row of threaded holes can include at most two threaded holes. In addition, while the plate is described as having two tabs, it will be appreciated that another number of tabs may be provided to the plate. For example, a single tab may be provided to the ulnar side of the head of the plate. It will therefore be appreciated by those skilled in the art that yet other modifications could be made to the provided invention without deviating from its spirit and scope as claimed.

What is claimed is:

1. A bone plate for a volar side of a distal end of a radius bone for use with a 1.6 mm K-wire, the distal radius bone having a diaphysis and a metaphysis, and the metaphysis having a volar rim, comprising:
   a) a bone contacting lower surface;
   b) an opposite upper surface;
   c) a shaft including a plurality of fastener holes to secure said shaft relative to the radius bone; and
   d) a head extending at a transverse orientation relative to said shaft, said head angled upwards relative to said shaft when said lower surface of said shaft is positioned substantially horizontal and face down, said head including a plurality of threaded holes, each defining a thread axis along which a fastener inserted into the threaded holes is retained along said thread axis, said head including a radial side and an ulnar side, said radial side tapering to a distal edge and being free and absent of any tab, and said ulnar side provided with a tab extending distally beyond said radial side distal edge, said tab provided with a K-wire hole with cylindrical sidewalls capable of closely receiving the 1.6 mm K-wire and retaining the K-wire in a fixed angle, said upper surface of said tab having a smooth contour with a tapered distal edge, a recess being provided to said lower surface of said bone plate and extending along an entire junction between said tab and a remainder of said head in alignment with said radial side distal edge to reduce a cross-sectional area moment of inertia thereat such that when the K-wire is inserted into said K-wire hole and a bending load is applied to the K-wire, said plate is bent at said reduced cross-sectional area to re-orient said tab about an axis in alignment with said radial side distal edge.

2. A bone plate according to claim 1, wherein:
said head includes two of said tabs extending from said ulnar side and extending beyond said radial side distal edge of said plate.

3. A bone plate according to claim 2, wherein:
said junctions between said tabs and said remainder of said head each having a width in a medial-lateral direction, and said width of said junctions not reduced relative to a remainder of said respective tabs.

4. A bone plate according to claim 2, wherein:
said junctions between said tabs and said remainder of said head each having a width in a medial-lateral direction, and said width of a remainder of said respective tabs not exceeding said width of said junctions.

5. A bone plate according to claim 1, wherein:
said threaded holes include a relatively proximal row of four threaded holes and a relatively distal row of at least two threaded holes, and
said tab is located distally in front of a medialmost of said at least two holes of said distal row, and
said head of said plate is provided with an adjacent intermediate tab located distally in front of a threaded hole of said distal row located adjacent said medialmost threaded hole of said distal row.

6. A bone plate according to claim 1, wherein:
said K-wire hole has an axis that is obliquely oriented relative to a lower surface of said plate at said tab.

7. A bone plate for a volar side of a distal end of a radius bone for use with a 1.6 mm K-wire, the distal radius bone having a diaphysis and a metaphysis, and the metaphysis having a volar rim, comprising:
   a) a bone contacting lower surface;
   b) an opposite upper surface;
   c) a shaft including a plurality of fastener holes to secure said shaft relative to the radius bone; and
   d) a head extending at a transverse orientation relative to said shaft, said head angled upwards relative to said shaft when said lower surface of said shaft is positioned substantially horizontal and face down,
      said head including a plurality of threaded holes, each defining a thread axis along which a fastener inserted into the threaded holes is retained along said thread axis, said threaded holes including a relatively proximal row of four threaded holes and a relatively distal row of at least two threaded holes, and
      said head including a radial side and an ulnar side, said radial side tapering to a distal edge, said ulnar side provided with first and second spaced apart tabs extending distally beyond said radial side distal edge,
      said tabs include an ulnar side tab located distally in front of a medialmost of said at least two holes of said distal row, and
      an adjacent intermediate tab located distally in front of a threaded hole of said distal row located adjacent said medialmost threaded hole of said distal row,
      each said tab provided with a K-wire hole with a cylindrical sidewall capable of closely receiving the 1.6 mm K-wire and retaining the K-wire in a fixed angle, said upper surface of each said tab having a smooth contour with a tapered distal edge, recesses being provided to said lower surface of said bone plate to extend along respective entire junctions between said first and second tabs and a remainder of said head in alignment with said radial side distal edge to reduce a cross-sectional area moment of inertia at said junctions, said junctions each having a width in a medial-lateral direction, said width of a remainder of said respective tabs not exceeding said width of said junctions,
      wherein when the K-wire is inserted into said respective K-wire holes and a bending load is applied to the K-wire, said plate is bent at said respective reduced cross-sectional areas to re-orient said respective tabs about an axis in alignment with said radial side distal edge.

8. A bone plate according to claim 7, wherein:
said K-wire hole has an axis that is obliquely oriented relative to a lower surface of said plate at said tab.

9. A bone plate according to claim 7, wherein:
said distal row includes three threaded holes.

10. A bone plate kit for use on a volar side of a distal end of a radius bone, the distal radius bone having a diaphysis and a metaphysis, and the metaphysis having a volar rim, comprising:
   a) 1.6 mm K-wire; and
   b) a bone plate having a bone contacting lower surface and an opposite upper surface, said bone plate including
      i) a shaft including a plurality of fastener holes to secure said shaft relative to the radius bone, and
      ii) a head extending at a transverse orientation relative to said shaft, said head angled upwards relative to said shaft when said lower surface of said shaft is positioned substantially horizontal and face down, said head including a plurality of threaded holes, each defining an thread axis along which a fastener inserted into the threaded holes is retained along said thread axis, said head including a radial side and an ulnar side, said radial side tapering to a distal edge, said ulnar side provided with a tab extending beyond said radial side distal edge, said tab provided with a K-wire hole with cylindrical sidewalls capable of closely receiving said K-wire and retaining said K-wire in a fixed angle, a recess provided to said lower surface of said bone plate along an entire junction between said tab and a remainder of said head and in alignment with said radial side distal edge to reduce a cross-sectional area moment of inertia thereat, wherein when said K-wire is inserted into said K-wire hole and a bending load is applied to said K-wire, said plate is bent at said reduced cross-sectional area to re-orient said tabs about respective axes in alignment with said radial side distal edge.

11. A bone plate kit according to claim 10, wherein:

said head includes two of said tabs extending from said ulnar side of said distal end head beyond said distal end of said side.

12. A bone plate kit according to claim 11, wherein:

said junctions between said tabs and said remainder of said head each having a width in a medial-lateral direction, and said width of said junctions not reduced relative to a remainder of said respective tabs.

13. A bone plate kit according to claim 11, wherein:

said junctions between said tabs and said remainder of said head each having a width in a medial-lateral direction, and said width of a remainder of said respective tabs not exceeding said width of said junctions.

14. A bone plate kit according to claim 10, wherein:

said threaded holes include a relatively proximal row of four threaded holes and a relatively distal row of at least two threaded holes, and said tabs include an ulnar side tab located distally in front of a medialmost of said three threaded holes of said distal row, and an adjacent tab located distally in front of a threaded hole in said distal row adjacent said medialmost threaded hole in said distal row.

15. A bone plate kit according to claim 14, wherein:

said distal row includes three threaded holes.

16. A bone plate kit according to claim 10, wherein:

said K-wire hole has an axis that is obliquely oriented relative to a lower surface of said plate at said tab.

17. A bone plate kit according to claim 10, further comprising:

a ⅜ inch circle suture needle and length of suture attached thereto, said K-wire hole in said tab located within said tab and sized to permit said suture needle to be passed completely therethrough.

18. A bone plate for use on a volar side of a distal end of a radius bone with a plurality of fasteners, the distal radius bone having a diaphysis and a metaphysis, and the metaphysis having a volar rim, comprising:

a rigid metal plate having a bone contacting lower surface and an opposite upper surface, said plate including a shaft including a plurality of fastener holes at which to secure said shaft relative to the radius bone which respective ones of the fasteners, and a head extending at a transverse orientation relative to said shaft, said head angled upwards relative to said shaft when said lower surface of said shaft is positioned substantially horizontal and face down, said head including a plurality of threaded holes, each defining an thread axis along which one of the fasteners inserted into the threaded holes is retained along said thread axis, said head including a radial side and an ulnar side, said radial side being free and absent of any tab and tapering to a distal edge, said ulnar side provided with a tab extending beyond said radial side distal edge, said tab provided with a cylindrical hole having non-threaded cylindrical sidewalls extending between the lower and upper surfaces, a recess provided to said lower surface of said bone plate along an entire junction between said tab and a remainder of said head and in alignment with said radial side distal edge to reduce a cross-sectional area moment of inertia thereat.

19. A combination of a bone plate and suture needle for use on a volar side of a distal end of a radius bone, the bone plate for use with a plurality of fasteners, the distal radius bone having a diaphysis and a metaphysis, and the metaphysis having a volar rim, comprising:

a rigid metal bone plate having a bone contacting lower surface and an opposite upper surface, said plate including a shaft including a plurality of fastener holes at which to secure said shaft relative to the radius bone which respective ones of the fasteners, and a head extending at a transverse orientation relative to said shaft, said head angled upwards relative to said shaft when said lower surface of said shaft is positioned substantially horizontal and face down, said head including a plurality of threaded holes, each defining an thread axis along which one of the fasteners inserted into the threaded holes is retained along said thread axis, said head including a radial side and an ulnar side, said radial side tapering to a distal edge, said ulnar side provided with a tab extending beyond said radial side distal edge, said tab provided with a cylindrical hole having non-threaded cylindrical sidewalls extending between the lower and upper surfaces, a recess provided to said lower surface of said bone plate along an entire junction between said tab and a remainder of said head and in alignment with said radial side distal edge to reduce a cross-sectional area moment of inertia thereat; and a curved suture needle and length of suture attached thereto, said cylindrical hole of said bone plate sized to permit said suture needle to be passed completely therethrough.

20. A bone plate and suture needle combination according to claim 19, wherein said suture needle is a ⅜ inch circle suture needle.

21. A combination of a bone plate and a K-wire for use on a volar side of a distal end of a radius bone, the bone plate for use with a plurality of fasteners, the distal radius bone having a diaphysis and a metaphysis, and the metaphysis having a volar rim, comprising:

a rigid metal bone plate having a bone contacting lower surface and an opposite upper surface, said plate including a shaft including a plurality of fastener holes at which to secure said shaft relative to the radius bone which respective ones of the fasteners, and a head extending at a transverse orientation relative to said shaft, said head angled upwards relative to said shaft when said lower surface of said shaft is positioned substantially horizontal and face down, said head including a plurality of threaded holes, each defining an thread axis along which one of the fasteners inserted into the threaded holes is retained along said thread axis, said head including a radial side and an ulnar side, said radial side tapering to a distal edge, said ulnar side provided with a tab extending beyond said radial side distal edge, said tab provided with a cylindrical hole having non-threaded cylindrical sidewalls extending between the lower and upper surfaces, a recess provided to said lower surface of said bone plate along an entire junction between said tab and a remainder of said head and in alignment with said radial side distal edge to reduce a cross-sectional area moment of inertia thereat; and a K-wire, wherein said cylindrical sidewalls of said tab capable of closely receiving said K-wire and retaining said K-wire in a fixed angle relative to said plate.

22. A bone plate according to claim 18, wherein said tab at said ulnar side is provided with at most a single hole.

23. A bone plate for a volar side of a distal end of a radius bone for use with a 1.6 mm K-wire, the distal radius bone having a diaphysis and a metaphysis, and the metaphysis having a volar rim, comprising:
  a) a bone contacting lower surface;
  b) an opposite upper surface;
  c) a shaft including a plurality of fastener holes to secure said shaft relative to the radius bone; and
  d) a head extending at a transverse orientation relative to said shaft, said head angled upwards relative to said shaft when said lower surface of said shaft is positioned substantially horizontal and face down, said head including a plurality of threaded holes, said threaded holes including a relatively proximal row of four threaded holes and a relatively distal row of at least two threaded holes, said distal row of threaded holes defining a medialmost threaded hole, each threaded hole defining a thread axis along which a fastener inserted into the threaded holes is retained along said thread axis, said head including a radial side and an ulnar side, said radial side tapering to a distal edge, and said ulnar side provided with (i) an ulnar side tab located distally in front of said medialmost threaded hole of said distal row and extending distally beyond said radial side distal edge, and (ii) an adjacent intermediate tab located distally in front of a threaded hole of said distal row located adjacent said medialmost threaded hole of said distal row and extending distally beyond said radial side distal edge, each said tab provided with a K-wire hole with cylindrical sidewalls capable of closely receiving the 1.6 mm K-wire and retaining the K-wire in a fixed angle, said upper surface of each said tab having a smooth contour with a tapered distal edge, a recess being provided to said lower surface of said bone plate and extending along an entire junction between said respective tab and a remainder of said head in alignment with said radial side distal edge to reduce a cross-sectional area moment of inertia thereat such that when the K-wire is inserted into said K-wire hole and a bending load is applied to the K-wire, said plate is bent at said reduced cross-sectional area to re-orient said tab about an axis in alignment with said radial side distal edge.

* * * * *